United States Patent [19]

Swearington

[11] Patent Number: 5,056,509

[45] Date of Patent: Oct. 15, 1991

[54] ANKLE BRACE

[76] Inventor: Derritt R. Swearington, 672 Forest Ave., Jackson, Miss. 39206

[21] Appl. No.: 640,148

[22] Filed: Jan. 11, 1991

[51] Int. Cl.[5] .......................... A61F 5/00; A43B 7/20
[52] U.S. Cl. ............................. 128/80 H; 128/80 R; 128/80 F; 36/89
[58] Field of Search ............... 128/80 H, 80 R, 80 E, 128/80 F, 83.5, 88, 166, 89 R; 36/89, 90, 119, 111.5

[56] References Cited

U.S. PATENT DOCUMENTS

| | | | |
|---|---|---|---|
| 1,205,206 | 11/1916 | Hofmeister | 36/89 |
| 3,805,773 | 4/1974 | Schau | 128/80 E |
| 4,510,927 | 4/1985 | Peter | 128/80 H |
| 4,665,904 | 5/1987 | Lerman | 128/80 H |
| 4,676,011 | 6/1987 | O'Rourke et al. | 36/89 |
| 4,922,630 | 5/1990 | Robinson | 36/89 |

Primary Examiner—Richard J. Apley
Assistant Examiner—Karen G. Horowitz
Attorney, Agent, or Firm—Larson & Taylor

[57] ABSTRACT

A foot and ankle brace is provided which is adapted to be worn within an athletic shoe to provide support for the foot and ankle while permitting limited inversion and eversion of the foot together with unlimited dorsiflexion and plantar flexion. There is provided an inner member including a foot plate which extends around the heel and protects the instep. An inner brace member comprising a U-shaped upper end portion engages the leg above the ankle and integrally formed with the U-shaped member are downwardly extending arms which are pivotally mounted on the upper edge portion of the foot plate. The inner brace is flexible so that it permits inversion and eversion of the foot as well as unlimited dorsiflexion and plantar flexion movement due to the pivotal joint in the inner member. An outer brace member formed of relatively rigid material has a stirrup which fits beneath the foot plate of the inner member and has a U-shaped brace member which fits over the brace member on the inner member and the outer member has a pair of integrally formed arms extending downwardly to a pivoted joint disposed over the pivoted joint in the inner member. The outer member is also provided with hinges on the downwardly extending arms hinges permit limited inversion and eversion movement of the foot.

14 Claims, 2 Drawing Sheets

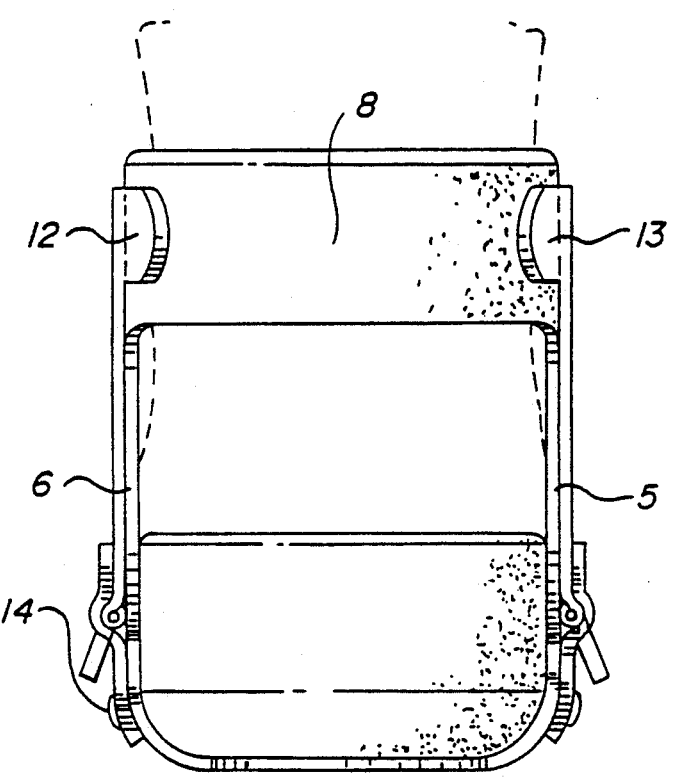
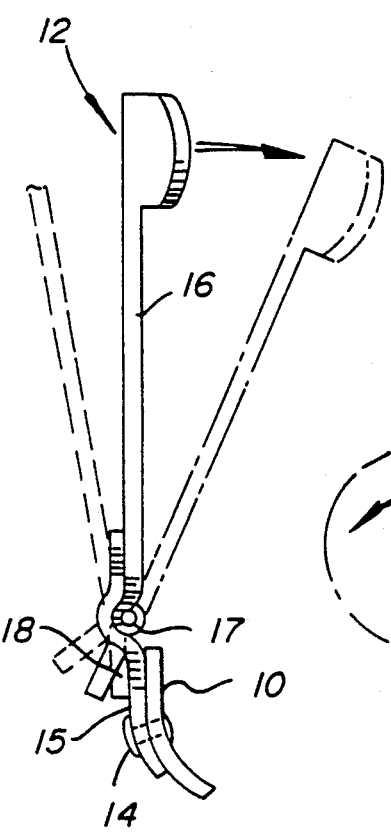
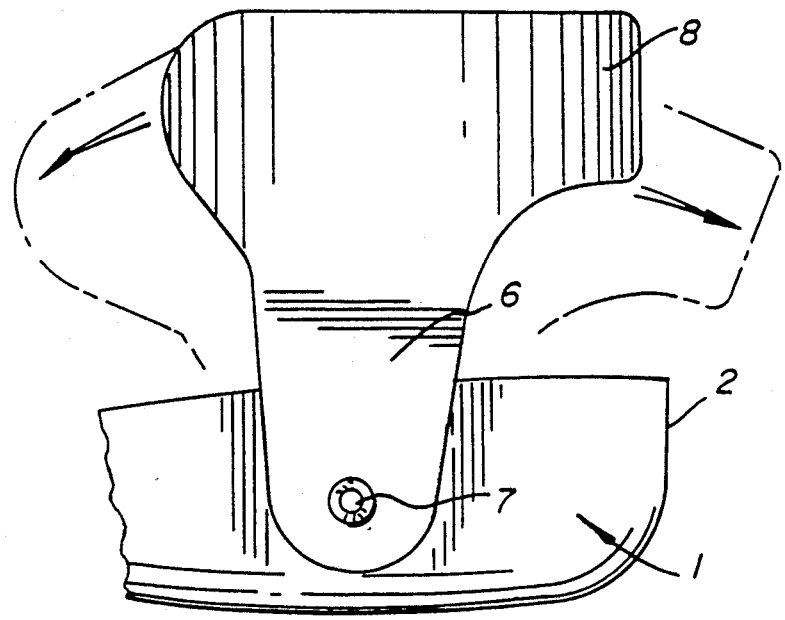
FIG. 3
FIG. 5
FIG. 4

ANKLE BRACE

FIELD OF THE INVENTION

The present invention relates to an orthodic device and more specifically to an ankle brace comprising a foot plate and a brace pivotally mounted on the foot plate which restricts the inversion and eversion of the ankle within acceptable limits to prevent damage to the ankle joint.

BACKGROUND OF THE INVENTION

There are in the prior art a number of ankle braces which have been developed for protecting the ankle from damage or for providing protection and support for an ankle fracture. In the latter case, devices such as shown in the Crispin U.S. Pat. No. 4,771,768 the Biedermann U.S. Pat. No. 4,834,078 and Spencer U.S. Pat. No. 4,630,600 have been developed to control the motion of the leg with respect to the foot to permit the injured ligaments or ankle fracture to heal. These devices are used when a plaster cast is removed from an injured ankle joint so as to provide some degree of freedom of movement.

There are prior art devices which are designed to provide support for the ankle to brace the ankle against lateral sprains. Examples of such devices are the Craythorne U.S. Pat. No. 4,865,023 and Robinson U.S. Pat. No. 4,922,630. The Craythorne provides a heel plate together with a bracing pad comprising an ankle cuff which fits around the leg portion and provides a method for bracing the ankle but does not permit sufficient angular motion of the ankle joint. The Robinson U.S. Pat. No. 4,922,630 provides an inversion resisting device which does permit motion in eversion, plantar flexion and dorsi flexion. The device provides a leg engaging strap which is connected to the shoe by a strapping mechanism.

Other patents showing various types of ankle support structures are the Sproaken U.S. Pat. No. 4,425,721, Rathmell U.S. Pat. No. 3,775,872, Ottieri U.S. Pat. No. 4,955,149 and Grim U.S. Pat. No. 4,869,267. All of these prior devices are designed to protect the ankle by limiting the degree of movement of the leg with respect to the foot so as to protect the ankle from fracture or sprains.

SUMMARY OF THE INVENTION

In accordance with the present invention, an ankle brace is provided which permits full normal flexion of the foot with respect to the leg. However, the device disclosed herein prevents inversion and eversion beyond acceptable limits. Thus, a brace is provided which fits within an athletic shoe so as to permit the wearer normal flexion of the foot but prevents inversion and eversion beyond predetermined angular limits so as to prevent ankle sprains and the like.

The present invention provides a foot plate which is shaped so as to support the heel and arch of the foot and extends forwardly to the metatarsal area. Pivotally mounted on the foot plate is a flexible brace member comprising arms extending upwardly with a cuff portion extending around the back of the leg above the ankle joint. A stirrup fits beneath the foot plate and has flanges extending upwardly on each side of the stirrup. Rigid T-shaped bars are pivotally mounted on the flanges to permit plantar and dorsi flexion of the foot. Hinge elements are provided on the T-shaped bars with limit stops so as to restrict the inversion and eversion angular movement of the foot within acceptable limits. Thus, normal flexion of the foot is virtually entirely unrestricted.

An object of the invention is to provide an ankle brace which permits normal flexion of the foot while providing support for the ankle.

A further object of the present invention is to limit inversion and eversion movement of the foot within acceptable limits while permitting complete normal flexion of the foot.

Other objects and many of the attendant advantages of the present invention will become readily apparent upon consideration of the following detailed specification together with the accompanying drawings.

BRIEF DESCRIPTION OF THE DRAWINGS

FIG. 3 is a rear elevational view of the ankle brace, FIG. 4 is a partial elevational view showing the angular movement of the inner ankle brace, and FIG. 5 is a elevational view of the outer brace member showing the limits of the angular movement.

DETAILED DESCRIPTION OF THE PREFERRED EMBODIMENTS

Figure 1:
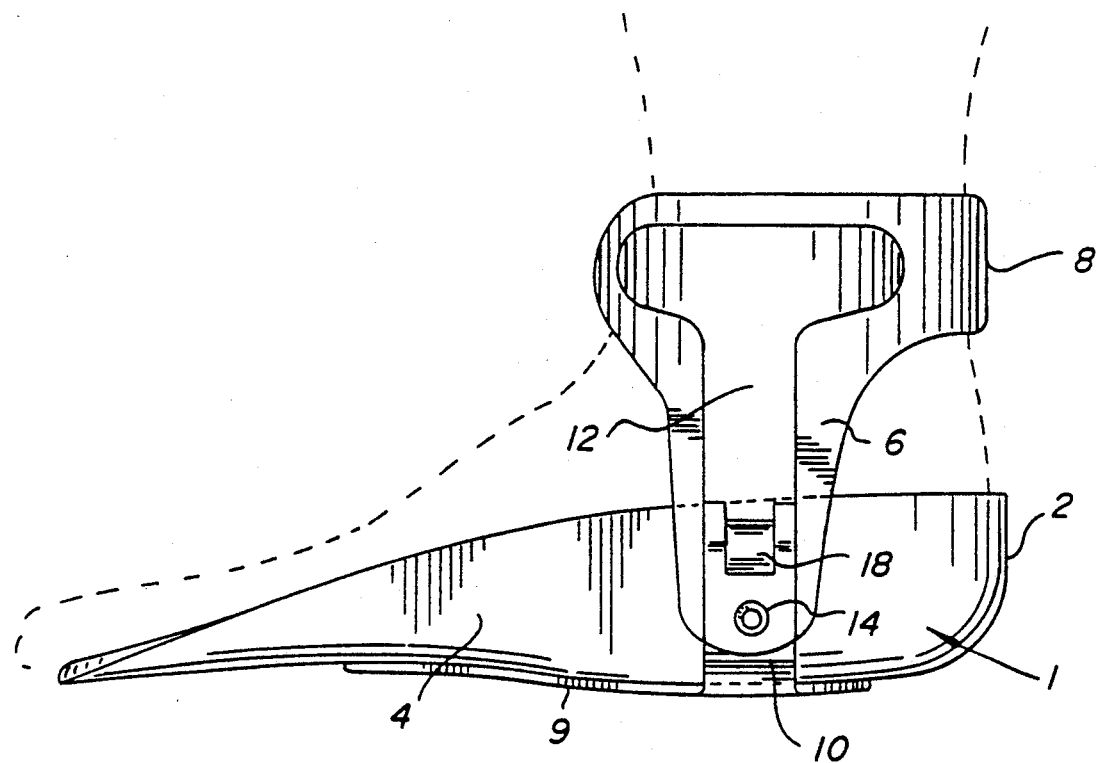
FIG. 1 is a side elevation of the ankle brace according to the present invention.
Figure 2:
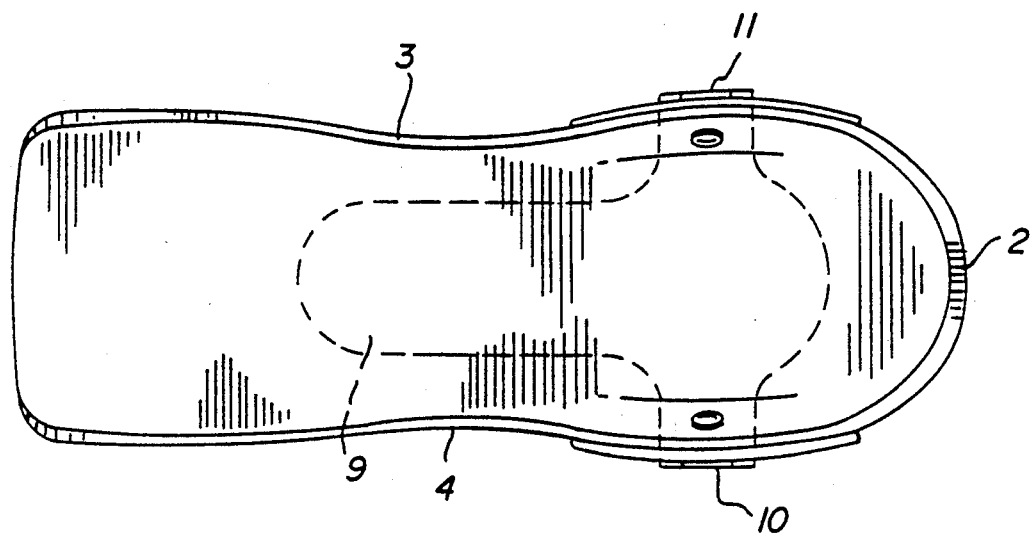
FIG. 2 is a top plan view of the ankle brace.

There is shown in FIG. 1 a foot plate 1 which is formed of a plastic material to conform to the shape of the foot of the user. The foot plate 1 includes an upwardly extending heel portion 2 which, as shown in FIG. 2 extends around the sides of the foot at 3 and 4 and is tapered downwardly toward the bottomwall of the foot plate at the forward end of the arch portion of the foot. The foot plate extends from the heel to a point adjacent the metatarsals.

As more clearly shown in FIGS. 3 and 4, there is provided an inner brace member having arms 5 and 6 pivotally mounted on the foot plate as shown at 7 in FIG. 4 so as to permit forward and rearward movement of the arms 5 and 6 with respect to the foot plate 1. The arms 5 and 6 have a U-shaped cuff portion 8 integrally formed therewith which extends around the rear portion of the leg above the ankle joint as shown in FIG. 1.

The inner ankle brace comprising the arms 5 and 6 and cuff portion 8 is formed of flexible plastic material so that in addition to the plantar and dorsi flexion provided by the pivot 7, the ankle brace may move laterally in inversion and eversion movements.

Secured to the bottom of the foot plate is a stirrup member 9 as shown in FIGS. 1 and 2. The stirrup member has a pair of flanges 10 and 11 extending upwardly from each side of the stirrup member as shown in FIG. 2 and T-shaped bars 12 and 13 forming outer brace members are pivotally mounted on the flanges 10 and 11 as shown at 14 in FIGS. 1 and 5. As seen in FIG. 5, the brace member 12 is formed in two sections. There is an end section 15 which is pivoted to the flange 10 by pivot 14 and an upper end section 16 which is connected with end portion 15 by means of a hinge 17. The hinge 17 permits inward and outward movement of the section 16 with respect to the section 15 and the upper end section 16 has a limit stop 18 as shown in FIGS. 1 and 5 which permits limited outward movement of the upper end section 16 by the abutment of the stop 18 with the outer face of lower end section 15. The T-bars 12 and 13 are constructed identically so that movement of the leg with respect to the foot in inversion and eversion is limited by means of the limit stops 18 on the hinges of the T-bar braces 12 and 13.

The pivot pins 7 on the inner brace member are aligned with the pivot pins 14 on the outer brace members so that full movement of the foot and leg in plantar flexion and dorsi flexion is permitted. However, movement of the foot in inversion and eversion is limited by the limit stops 18 on the hinge members of the outer brace members 12 and 13. The brace members 12 and 13 are of rigid material such as metal and may be secured to the inner brace members in any desired manner, such as, for example, by glue or pins between the inner and outer members.

The brace members disclosed herein may fit within an athletic shoe and permit full movement of the foot in plantar and dorsi flexion while limiting the angular movement in inversion and eversion within predetermined angles. A maximum desired inversion movement is 20° while a maximum eversion is approximately 10°. It should be noted that straps (not shown) are provided to retain the foot plate and ankle brace snugly on the foot portion and leg of the wearer.

Obviously, many modifications and variations of the present invention are possible in light of the above teachings.

What is claimed as new and is desired to be secured by Letters Patents is:

1. An ankle brace comprising, in combination, a foot plate, means for supporting the ankle comprising a pair of upwardly extending arms pivotally mounted on the sides of said foot plate at the lower ends of the arms to permit forward and rearward motion of the arms with respect to the foot plate, said pair of arms being flexible to permit lateral movement of the arms with respect to the foot plate, upwardly extending means overlying the outer faces of the upwardly extending portions of said arms and pivotally mounted on said foot plate, said upwardly extending means including means for limiting the lateral movement of the arms with respect to the foot plate and means on the upper ends of the arms to engage the leg of the wearer.

2. An ankle brace according to claim 1 wherein the pivotal mounting between the arms and foot plate is directly below the ankle of the wearer.

3. An ankle brace according to claim 1 wherein the means on the upper ends of the arms to engage the leg of the wearer comprises a U-shaped generally horizontal bar integrally formed with said pair of arms, said U-shaped bar extending around the back of the leg of the wearer.

4. An ankle brace according to claim 1 wherein said means on the outer faces of said arms for limiting the lateral movement of the arms with respect to the foot plate comprises a pair of braces extending contiguously with the outer faces of said arms, and further including hinge means on said braces, said hinge means having limit stops thereon to prevent lateral movement of said arms with respect to said foot plate beyond a predetermined angle.

5. An ankle brace according to claim 4 wherein said braces are made of a nonflexible material.

6. An ankle brace according to claim 4 wherein said hinge means with limit stops permits lateral movement of the leg with respect to the foot of the wearer up to 20° inversion and 10° eversion.

7. An ankle brace according to claim 4 wherein said means for limiting the lateral movement of the arms with respect to the foot plate further comprises a stirrup extending beneath the foot plate, said stirrup having an upwardly extending flange on each side of said stirrup, means for pivotally mounting said braces on said flanges to permit forward and rearward movement of said braces.

8. An ankle brace according to claim 1 wherein said foot plate extends upwardly around the heel of the foot and extends forwardly adjacent the metatarsal joints.

9. An ankle brace according to claim 1 wherein said foot plate includes integrally formed extensions on each side of the foot plate beneath the ankle of the wearer, said arms being pivotally mounted on said extensions.

10. A brace to be fitted on the foot and leg to provide support for the ankle, comprising, in combination, a foot plate, a pair of arms pivotally mounted on said foot plate beneath the ankle, the upper ends of the arms being interconnected with a U-shaped member extending around the back of the leg, said arms being flexible to provide for lateral movement of the leg with respect to the foot, the pivotal mounting of the arms with respect to the foot plate permitting forward and rearward movement of the leg with respect to the foot and upwardly extending means pivotally mounted on the foot plate and overlying said upper ends of said arms, said upwardly extending means including means for limiting the lateral movement of the leg with respect to the foot.

11. A brace according to claim 10 wherein said last named means comprises a pair of members extending substantially parallel to said arms, hinge means on said members, said hinge means having limit stops thereon to prevent lateral movement of said arms with respect to said foot plate beyond a predetermined angle.

12. A brace according to claim 11 wherein said hinge means with limit stops permits lateral movement of the leg with respect to the foot up to 20° inversion and 10° eversion.

13. A brace according to claim 11 and further including a stirrup extending beneath the foot plate, said stirrup pivotally mounting said member to permit forward and rearward movement of said members with respect to the foot plate.

14. A brace according to claim 13 wherein said pivotal mountings of said stirrup and said members are disposed immediately adjacent the pivotal mountings of the arms and foot plate.

* * * * *